(12) United States Patent
Hultmark et al.

(10) Patent No.: US 9,500,615 B2
(45) Date of Patent: Nov. 22, 2016

(54) FAST RESPONSE HUMIDITY SENSOR

(71) Applicants: Marcus Hultmark, Princeton, NJ (US); Gilad Arwatz, Princeton, NJ (US); Yuyang Fan, Princeton, NJ (US); Margit Vallikivi, Princeton, NJ (US)

(72) Inventors: Marcus Hultmark, Princeton, NJ (US); Gilad Arwatz, Princeton, NJ (US); Yuyang Fan, Princeton, NJ (US); Margit Vallikivi, Princeton, NJ (US)

(73) Assignee: THE TRUSTEES OF PRINCETON UNIVERSITY, Princeton, NJ (US)

(*) Notice: Subject to any disclaimer, the term of this patent is extended or adjusted under 35 U.S.C. 154(b) by 192 days.

(21) Appl. No.: 14/456,614

(22) Filed: Aug. 11, 2014

(65) Prior Publication Data

US 2015/0075280 A1 Mar. 19, 2015

Related U.S. Application Data

(60) Provisional application No. 61/864,127, filed on Aug. 9, 2013.

(51) Int. Cl.
*G01N 19/00* (2006.01)
*G01N 27/12* (2006.01)

(52) U.S. Cl.
CPC .......... *G01N 27/121* (2013.01); *G01N 27/125* (2013.01); *Y10T 29/49085* (2015.01)

(58) Field of Classification Search
CPC .............. G01N 27/048; G01N 27/121; G01N 27/125

USPC ................. 73/29.02, 335.02, 335.03, 335.05
See application file for complete search history.

(56) References Cited

U.S. PATENT DOCUMENTS 4,419,888 A * 12/1983 Kitamura ............... G01N 25/64
73/23.21
4,793,181 A * 12/1988 Djorup ................. G01N 27/121
73/29.02

OTHER PUBLICATIONS

Kimura et al. "A new type humidity sensor using micro-air-bridge heaters;" Microsystems Technologies, 1995.*
(Continued)

*Primary Examiner* — Benjamin Schmitt
(74) *Attorney, Agent, or Firm* — Meagher Emanuel Laks Goldberg & Liao, LLP (57) ABSTRACT

A water content sensor is disclosed. The sensor includes a wire filament configured with a Péclet number of 1 or less. The wire filament has an electrically conductive material with an electrical resistance that varies as a function of temperature. The sensor includes a pair of electrically conductive prongs coupled to opposite ends of the wire filament. Electrically conductive stubs may be coupled to the prongs. A structural support may be coupled to the prongs. The structural support structure may be comprised of silicon. The wire filament may be coupled to driving circuitry configured to supply an electric current to the wire filament to maintain the wire filament at one of an approximately constant current, an approximately constant voltage and an approximately constant temperature. The wire filament may be platinum or titanium.

21 Claims, 12 Drawing Sheets

(56) References Cited

OTHER PUBLICATIONS

Bailey et al., "Turbulence measurements using a nanoscale thermal anemometry probe" Journal of Fluid Mechanics. vol. 663, pp. 60-179, 2010.
Vallikivi et al., "Turbulence measurements in pipe flow using a nano-scale thermal anemometry probe" Experiments in Fluids, vol. 51, pp. 1521-1527, 2011.

* cited by examiner

FAST RESPONSE HUMIDITY SENSOR

CROSS-REFERENCE TO PRIOR FILED APPLICATIONS

This application claims the benefit of U.S. Provisional Application No. 61/864,127, filed Aug. 9, 2013, which is incorporated herein in its entirety.

TECHNICAL FIELD

The present disclosure generally relates to measurement of water content in a gas sample, e.g., humidity and more particularly fast-response, small-size, sensors configured for high frequency measurements over a broad range of water content and temperature.

BACKGROUND OF THE INVENTION

Atmospheric turbulence is characterized by extremely high Reynolds numbers, which implies a very large range of scales present in the flow. The largest scales are on the order of 1 km and the smallest on the order of 1 mm. Conducting experiments in such conditions is very complicated since all scales need to be resolved. This implies long sample times, at high sample rates using small sensors. The size of the sensor needs to be on the order of the smallest scales, or smaller, and the bandwidth needs to be higher than the frequency corresponding to that of the smallest eddies. A windy day the wind speed typically is 10 m/s which, according to Taylor's frozen field hypothesis, will result in frequencies up to 10 kHz. Traditionally the bandwidth for sensors used in the atmosphere are much lower than that, but efforts have been made to resolve the complete frequency spectrum for the turbulent velocity field with fast-response velocity sensors, that can survive the rough conditions they are exposed to in the atmosphere.

In order to accurately predict the energy balance at the earth's surface, a critical component to any weather prediction or climate model, one needs information about the scalar fields in addition to the velocity field. The scalar fields of interest are mainly temperature and humidity, since those constitute the main contributions of heat fluxes away from the surface due to the atmospheric flow. The sensible heat flux is the covariance between the temperature field and the velocity component normal to the surface, $\overline{\omega'\theta'}$, which corresponds to the energy transferred away from the surface, in form of temperature. The latent heat flux is the covariance between the same velocity component and the humidity field, $\overline{\omega'q'}$, which is the part of the energy carried into the atmosphere by evaporation of water at the surface. The ability to predict these fluxes will allow closure to the governing equations, which is the purpose of turbulence models.

Unfortunately, the two covariances are very challenging to measure experimentally, and only the equations for very low Reynolds can be solved numerically. Two methods are commonly used to measure humidity in the air: laser based and capacitance based sensors. A fast response laser based system is typically too expensive to densely instrument test sites (even the conventional slow response systems are very expensive). Capacitance based systems will always have a time response several order of magnitudes too slow, since it takes time to replenish the cavity between the electrodes.

Another method to measure humidity is to measure the thermal conductivity of the air, which is a function of humidity. Sensors based on this technique have been tested and shown to work well. Unfortunately, distinguishing the sensitivity of humidity from air velocity is difficult using this method, since both act to increase the heat transfer from a heated element. The currently available techniques for measuring humidity are neither fast nor small enough to capture small scale turbulent fluctuations.

In addition, in some fields, accurate measurement of low humidity levels is critical, such as in the natural gas industry. There, water vapor must be removed from the gas stream in order to prevent problems relating to the processing, storage, and transportation of natural gas—water can lead to corrosion and/or the formation of hydrates. Additionally, there are often statutory or contractual limits to the water vapor concentration in gases; in the United States the maximum absolute humidity for interstate transfer of natural gas is set at 7 pounds per million standard cubic feet. Further due to the explosive or flammable nature of some gases, some measurement techniques cannot be utilized. The sensors that have been developed are therefore typically either cannot be used in hazardous areas, are very expensive, have significant response times, and/or are subject to drift over time.

Therefore, there is an acute need for fast-response, small-size, humidity sensors that can be used in the field over a broad range of humidity and temperature.

BRIEF SUMMARY OF THE INVENTION

A water content sensor is disclosed. The sensor includes a wire filament configured with a Péclet number of 1 or less. The wire filament has an electrically conductive material with an electrical resistance that varies as a function of temperature. The sensor includes a pair of electrically conductive prongs coupled to opposite ends of the wire filament. Electrically conductive stubs may be coupled to the prongs. A structural support may be coupled to the prongs. The structural support structure may be comprised of silicon. The wire filament may be coupled to driving circuitry configured to supply an electric current to the wire filament to maintain the wire filament at one of an approximately constant current, an approximately constant voltage and an approximately constant temperature. The wire filament may be platinum or titanium.

The wire filament may have has at least one of a circular and rectangular cross section. The wire filament may have a Péclet number of less than or equal to 0.1. The wire filament may have a characteristic length that is less than or equal to about 800 nm. The wire filament may have a characteristic length that is less than or equal to about 300 nm. The wire filament has a characteristic length that is less than or equal to about 100 nm. The prongs may be tapered or shaped on one end to reduce aerodynamical interference. The sensor may be combined with a second sensor having a second pair of electrically conductive prongs, the sensor being coupled to the second sensor by an electrically insulating connecting substrate. The connecting substrate may have opposite sides, each side being formed with electrical connections that are electrically coupled to the pair of electrically conductive prongs and second pair of electrically conductive prongs respectively. The electrically insulating connecting substrate may have a thickness of less than 300 μm. The first sensor may be configured to detect water content and the second sensor may be configured to detect one of temperature and velocity. The first sensor and second sensor may be configured with wire filaments that are oriented in a non-collinear orientation.

A system for measuring water content and temperature and/or velocity in a gas sample is also disclosed. The system includes a first sensor with a first wire filament configured with a Péclet number of 1 or less. The wire filament has an electrically conductive material with an electrical resistance that varies as a function of temperature. The first sensor includes a pair of electrically conductive prongs coupled to opposite ends of the wire filament. The system also has a second sensor comprising a second wire filament comprised of an electrically conductive material having an electrical resistance which varies as a function of temperature. An electrically insulating connecting substrate configured with electrical contacts is coupled to the first and second sensors. The electrically insulating connecting substrate configured may have a thickness of less than 300 µm. The first sensor may be configured to detect water content and the second sensor may be configured to detect one of temperature and velocity. The first sensor and second sensor may be configured with wire filaments that are oriented in a non-collinear orientation.

A method of forming a water content sensor is also disclosed. The method includes forming a wire filament configured with a Péclet number of 1 or less, the wire filament being comprised of an electrically conductive material having an electrical resistance which varies as a function of temperature. A wire filament is coupled to a pair of electrically conductive prongs coupled to opposite ends of the wire filament. Electrically conductive stubs may be coupled to the prongs. A structural support may be coupled to the prongs. The structural support structure may be comprised of silicon. The wire filament may be coupled to driving circuitry configured to supply an electric current to the wire filament to maintain the wire filament at one of an approximately constant current, an approximately constant voltage and an approximately constant temperature. The wire filament may be platinum or titanium.

The wire filament may be formed with at least one of a circular and rectangular cross section. The wire filament may have a Péclet number of less than or equal to 0.1. The wire filament may have a characteristic length that is less than or equal to about 800 nm. The wire filament may have a characteristic length that is less than or equal to about 300 nm. The wire filament has a characteristic length that is less than or equal to about 100 nm. The prongs may be tapered or shaped on one end to reduce aerodynamical interference. The sensor may be combined with a second sensor having a second pair of electrically conductive prongs, the sensor being coupled to the second sensor by an electrically insulating connecting substrate. The connecting substrate may have opposite sides, each side being formed with electrical connections that are electrically coupled to the pair of electrically conductive prongs and second pair of electrically conductive prongs respectively. The electrically insulating connecting substrate configured may have a thickness of less than 300 µm. The first sensor may be configured to detect water content and the second sensor may be configured to detect one of temperature and velocity. The first sensor and second sensor may be configured with wire filaments that are oriented in a non-collinear orientation.

A Nano Scale Thermal Anemometry Probe (NSTAP) sensing system is disclosed. The system includes a first Nano NSTAP sensor having a wire filament being comprised of an electrically conductive material having an electrical resistance which varies as a function of temperature a first pair of electrically conductive prongs coupled to opposite ends of the wire filament. The system also includes a second NSTAP having a wire filament being comprised of an electrically conductive material having an electrical resistance which varies as a function of temperature a first pair of electrically conductive prongs coupled to opposite ends of the wire filament. The first NSTAP sensor being coupled to the second NSTAP sensor by an electrically insulating connecting substrate. At least one of the first and second NSTAP sensor may include a wire filament configured with a Péclet number of 1 or less. The first and second NSTAP sensors may be configured to detect one of temperature and velocity. The first NSTAP sensor may be configured to detect temperature and the second NSTAP sensor may be configured to detect velocity.

A method of detecting water content in a fluid flow is also disclosed. The method includes establishing a current flow in a wire filament in a first sensor, the wire filament being configured with a Péclet number of 1 or less, the wire filament being comprised of an electrically conductive material having an electrical resistance which varies as a function of temperature. The wire filament is disposed in the fluid flow. The method also includes measuring at least one of a voltage across and current flowing through the wire filament. At least one of the measured voltage or current is correlated to a parameter under test using previously stored sensor characteristics.

Electrically conductive stubs may be coupled to the wire filament. A structural support may be coupled to the wire filament. The structural support structure may be comprised of silicon. The wire filament may be coupled to driving circuitry configured to supply an electric current to the wire filament to maintain the wire filament at one of an approximately constant current, an approximately constant voltage and an approximately constant temperature. The wire filament may be platinum or titanium.

The wire filament may have has at least one of a circular and rectangular cross section. The wire filament may have a Péclet number of less than or equal to 0.1. The wire filament may have a characteristic length that is less than or equal to about 800 nm. The wire filament may have a characteristic length that is less than or equal to about 300 nm. The wire filament has a characteristic length that is less than or equal to about 100 nm. The prongs may be tapered or shaped on one end to reduce aerodynamical interference. The sensor may be combined with a second sensor having a second pair of electrically conductive prongs, the sensor being coupled to the second sensor by an electrically insulating connecting substrate. The connecting substrate may have opposite sides, each side being formed with electrical connections that are electrically coupled to the pair of electrically conductive prongs and second pair of electrically conductive prongs respectively. The electrically insulating connecting substrate may have a thickness of less than 300 µm. The first sensor may be configured to detect water content and the second sensor may be configured to detect one of temperature and velocity. The first sensor and second sensor may be configured with wire filaments that are oriented in a non-collinear orientation.

DETAILED DESCRIPTION OF THE INVENTION

The disclosed humidity sensors are based on the Nano Scale Thermal Anemometry Probe (NSTAP), a sensor developed at Princeton University which can measure very small scale turbulent velocity fluctuations. The NSTAP has proven extremely useful in the study of turbulence in laboratory environment, due to its miniature size and extremely high bandwidth. What makes the NSTAP technology very attractive for atmospheric measurements is the high degree of flexibility in the design and manufacturing process. Sensors can easily be customized to meet the requirements in terms of spatial and temporal resolution, for a low cost.

While current NSTAP techniques can only measure velocity or temperature, by continuing to miniaturize the sensor, the embodied sensor becomes less sensitive to velocity fluctuations and can begin to measure humidity. This effect is due to low Péclet number, which implies that the heat transfer due to convection is less than that due to conduction to the air. It should be understood that the Péclet number (Pe) is a dimensionless number that is relevant in the study of transport phenomena in fluid flows. The Péclet number is generally defined to be the ratio of the rate of advection of a physical quantity by the flow to the rate of molecular diffusion of the same quantity driven by an appropriate gradient. The Péclet number typically has to be greater than unity in order to be sensitive to velocity changes. By utilizing designs having Péclet numbers of 1 or less, the disclosed sensors ensure that the signal generated is driven primarily by conductive effects, which are strongly correlated with humidity levels. It should be understood that the devices and methods disclosed herein are applicable to measurement of water content in air (humidity) as well as detection of water content in a wide variety of other gasses including but not limited to natural gas as discussed below.

A low Péclet number can be controlled by reducing the width of the wire used in the embodied sensors. For example, a device with a platinum wire filament having a cross-section measuring 100×100 nm was manufactured using electron beam lithography. It should be understood that other standard semi-conductor or MEMS fabrication techniques may also be used.

Results using the 100×100 nm version of this device in a wind tunnel indicate that it is insensitive to velocities up to about 10 m/s. However, the wire will still be sensitive to humidity fluctuations since they will affect the molecular heat diffusivity of air. By keeping the platinum sensing element at a constant temperature, using a circuit similar to those used for constant temperature hot-wire anemometry (see e.g., FIG. 2—reference number 214), the required instantaneous voltage over the wire will depend on the thermal conductivity of the air surrounding the wire, which allows for fast response humidity measurements. Tests conducted in a humidity chamber, without an imposed velocity, showed that a sensor with a sensing element of 100 nm×2 µm is sensitive to changes in humidity with an acceptable signal to noise ratio.

Figure 1A:
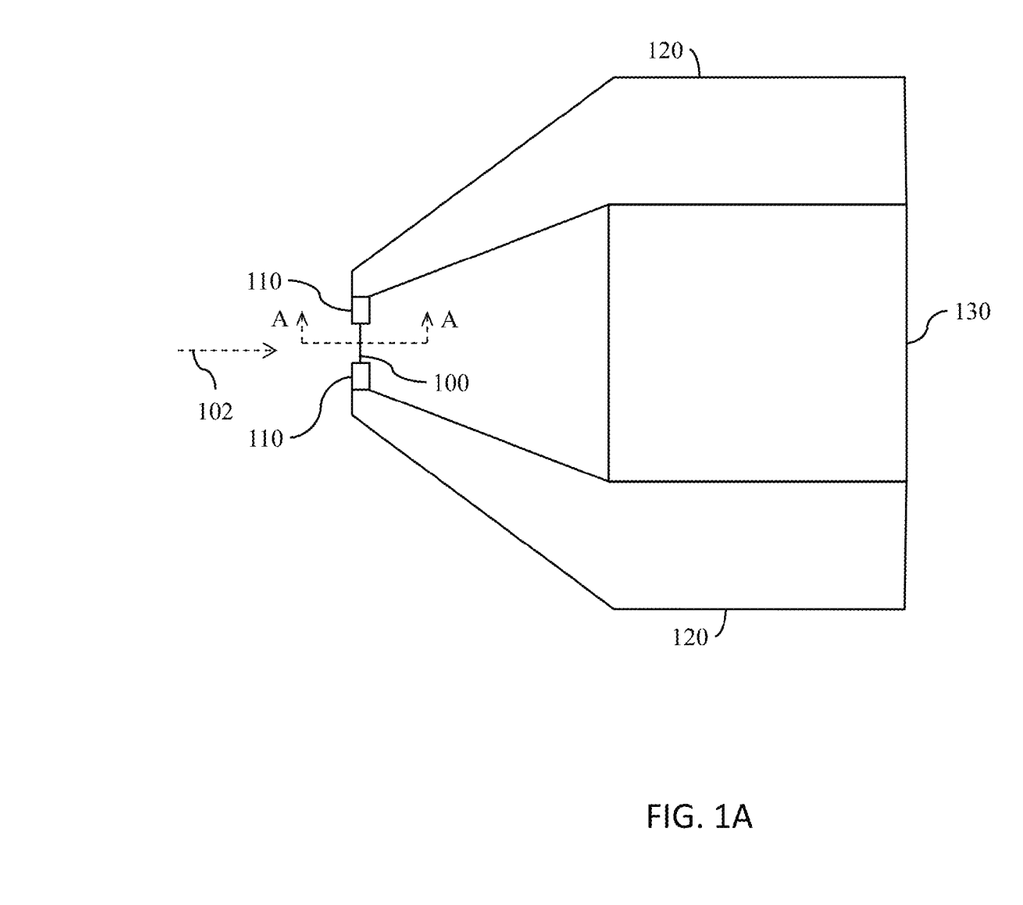
FIG. 1A is a block diagram showing a top view of a Nano Scale Thermal Anemometry Probe (NSTAP) sensor.
Figure 1B:
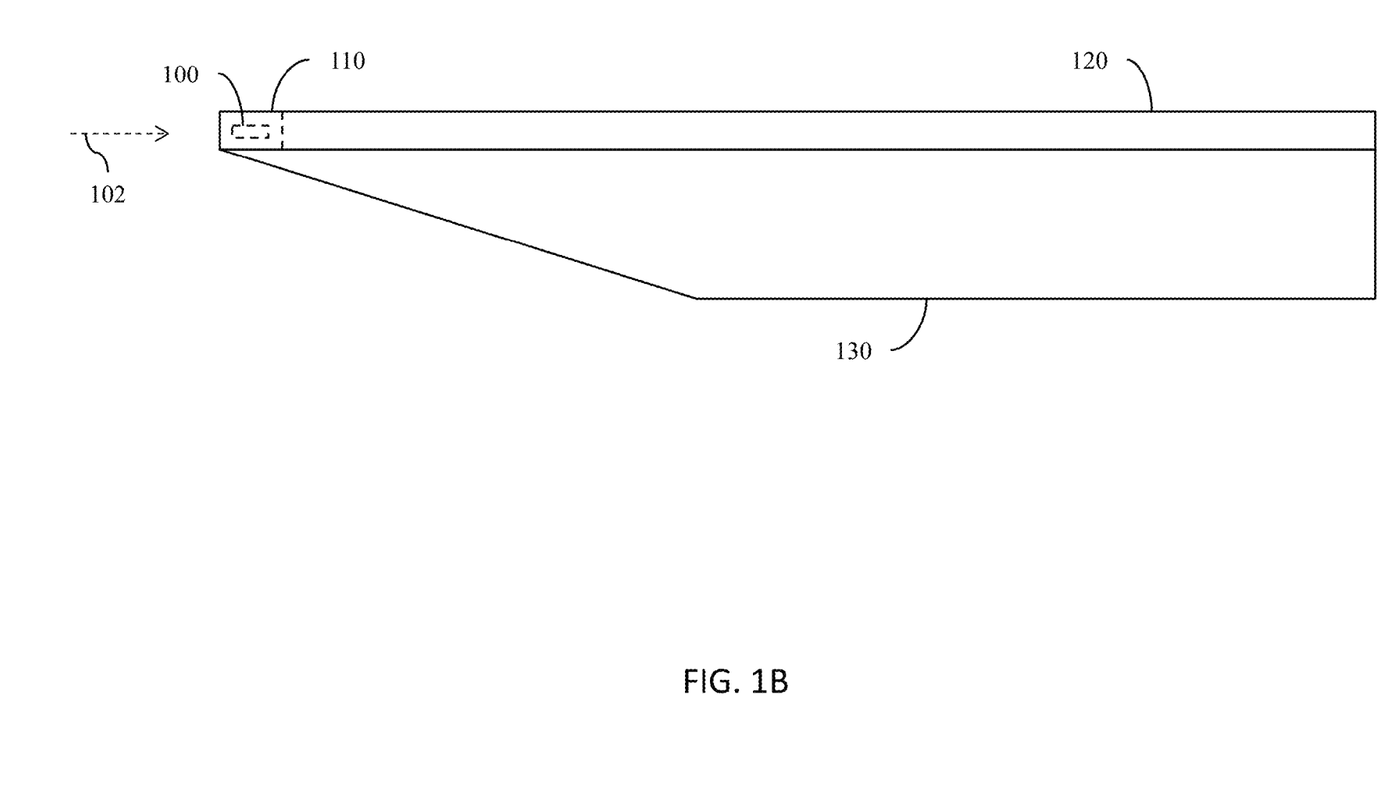
FIG. 1B is a side view of the NSTAP sensor of FIG. 1A.

FIG. 1A is a block diagram showing a top view of an embodiment of a NSTAP humidity sensor. FIG. 1B is a side view of the NSTAP humidity sensor of FIG. 1A. The humidity sensor is generally formed on a structural support 130 which may also act as a thermal buffer. Electrical supports or prongs 120 are coupled to a structural support 130. Structural support 130 may be formed of a variety of materials that are electrically insulated, e.g., silicon with silicon oxide insulator. Prongs 120 are configured to support a wire filament 100 that is generally attached to prongs 120. Wire filament 100 is generally exposed to fluid flow or airflow having a direction as generally shown by line 102.

The sensor may optionally include stubs 110. In this case the wire filament 100 is coupled to the stubs 110 and the stubs 110 are coupled to the prongs 120. In the alternative, the stubs 110 may be omitted and the wire filament 100 may be directly attached to the prongs 120. It should be understood that the structural support 130 may have a variety of geometric profiles without departing from the scope of this disclosure. In this example, the structural support 130 is generally tapered in the direction of fluid flow 102. It should also be understood that the structural support 130 may underlie at least a portion of the prongs 120.

The wire filament 100 is generally comprised of an electrically conductive material whose resistance varies as a function of temperature. The electrically conductive material is typically platinum, but depending on the design parameters or the environment in which the sensor is to be used, other materials or alloys may be used without departing from the scope of this disclosure.

Figure 1C:
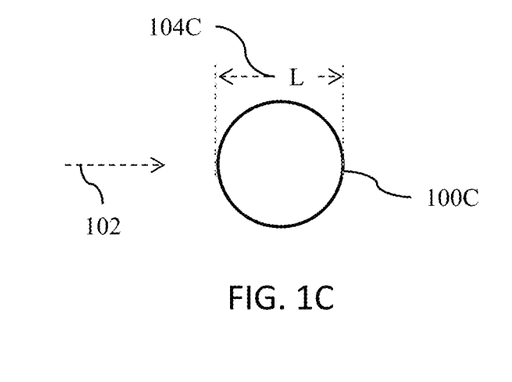
FIG. 1C is a cross sectional view of a wire filament taken across section A-A in FIG. 1A and having a circular profile.
Figure 1D:
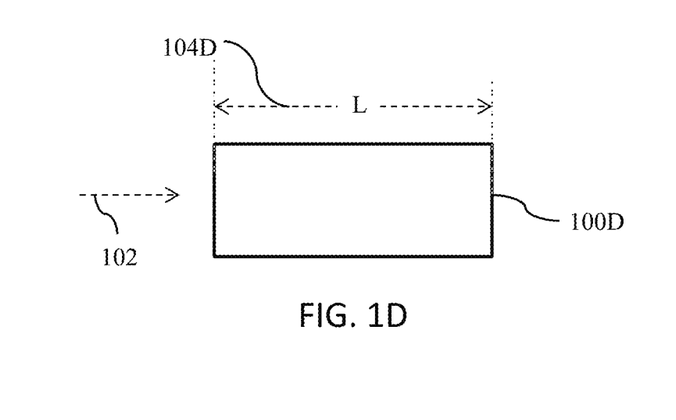
FIG. 1D is a cross sectional view of a wire filament taken across section A-A in FIG. 1A and having a rectangular profile.

The wire filament 100 is designed such that the characteristic length "L" is sufficiently small to allow diffusion to dominate the conduction for the given system. The characteristic length is generally the thickness of the wire filament that is oriented collinear with the direction of fluid flow. It should be understood that the wire filament 100 may have a variety of geometric profiles. For example, FIG. 1C is a cross sectional view of a wire filament 100C taken across section A-A in FIG. 1A and having a circular profile with a characteristic length 104C. FIG. 1D is a cross-sectional view of a wire filament 100D taken across section A-A in FIG. 1A and having a rectangular profile with a characteristic length 104D. It should be understood that other geometric profiles may be used without departing from the scope of this disclosure. For many humidity sensing applications, a characteristic length of less than 1 µm is likely sufficient. For others, a characteristic length of approximately 100 nm or less may be required. For example, a wire with a characteristic length of 1 µm may be sufficient for a particular system having an air velocity of 1 m/s, or a sheltered measurement location, but if the system instead has air velocities on the order of or greater than 10 m/s, a wire with a characteristic length of 100 nm may be appropriate. The length of the filament should be appropriate for the application, and should be sufficiently long so as to avoid end conduction effects. For most configurations, a length of around 60 µm or less is typical, although wire filaments with lengths of 10 µm or less may be necessary depending on spatial limitations of the sensor or structural limits of the materials.

If a stub 110 is used it will typically be comprised of an electrically conductive material, but not necessarily the same composition as that of the wire filament. If a stub is used, it will typically be at least as wide and as deep as the wire filament. There is no length limitation; for example, in one set of sensors, the length of the stubs was increased as the length of the filament wire was decreased in order to keep the prongs in the same location, thus maintaining the same sensor footprint. Further, it may be beneficial to minimize the thickness of the stubs to reduce aerodynamical interference in and around the wire filament.

The prongs 120 are generally comprised of an electrically conductive material, not necessarily the same composition as that of the wire filament. The prongs 120 are typically longer relative to their width or diameter. For example, in one sample configuration, the prongs 120 are approximately 5 mm long, while being less than 1 mm wide and 0.5 mm deep. In addition, the prongs 120 may be comprised of a substrate underlying the electrically conductive material. For example, the prongs 120 may be formed of a platinum layer deposited on a silicon structural support. Further, to minimize aerodynamical influence, the structural support and/or the prongs 120 may be tapered or shaped on the end attached to the stubs or filament. It should be understood that the prongs 120 may be deposited on or otherwise coupled to the structural support.

In some applications a single sensor may not provide sufficient information as the measurement of temperature and/or fluid velocity may also be required. For example, a system may be required to measure temperature, velocity, and humidity in a measurement volume of less than 1 mm$^3$, e.g., 60 µm$^3$. Previously available sensors cannot simply be stacked tightly together, as either aerodynamical interference, such as turbulence, generated from one sensor will interfere with another, or the electrically conductive elements will come in contact with each other, thus generating false sensor readings, or their physical size does not allow them to be stacked within such a small volume. Therefore, an approach for combining two or more small-size sensors such that the separation between the sensors is minimized is required.

Figure 2:
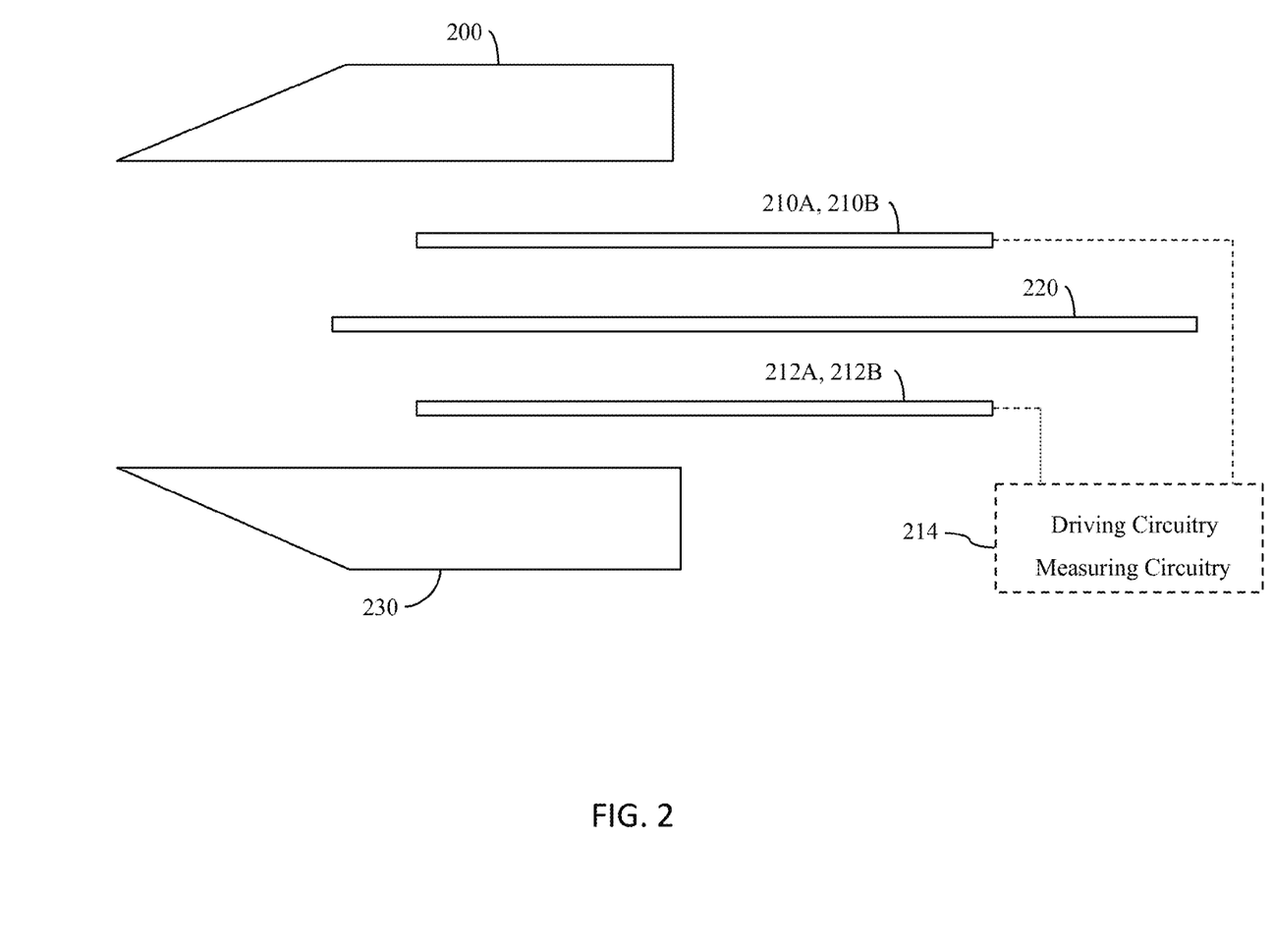
FIGS. 2-3 are illustrations of combining multiple NSTAP sensors.
Figure 3:
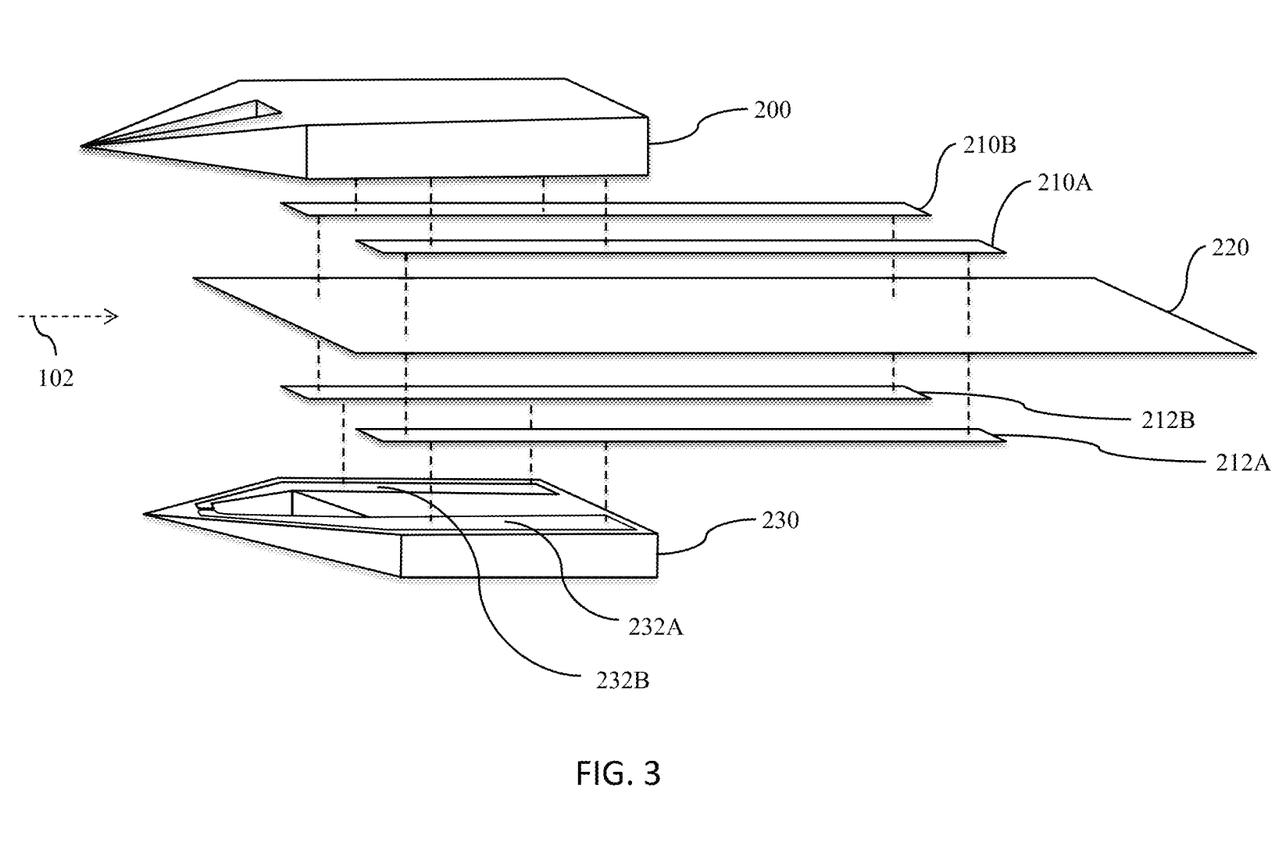

FIGS. 2 and 3 illustrate examples of combining multiple NSTAP sensors. In this example, the two NSTAP sensors have wire filaments that are generally collinear in orientation. Two pairs of electrical connections 210A and 210B, 212A and 212B are formed on or applied to both sides of a thin electrically insulating coupling substrate 220 (typically a film). The coupling substrate may be of any material appropriate for the design environment, such as a polyimide. NSTAP sensor 200 and NSTAP sensor 230 are then attached to the substrate, with a given sensor's prongs making contact with the connections on that side of the substrate.

As shown in FIG. 3, the pairs of electrical connections 210A and 210B are formed on a first side of the electrically insulating connecting substrate 220. The electrical connections 210A and 210B are spaced apart sufficiently so first connection 210A will touch a first prong of first sensor 200, and second connection 210B will touch a second prong of the first sensor 200. On the second side of the substrate, the second set of electrical connections 212A and 212B are also placed sufficiently far apart such that first connection 21A touches first prong 232A on second sensor 230. The second trace 212B touches second prong 232B on the second sensor 230.

In such a configuration, the separation between the sensors is largely determined by the thickness of the connecting substrate 220. This thickness may be generally between about 25 µm and about 125 µm, and varies depending on the characteristics required of the connecting substrate.

In one example, ultra-smooth 50 µm Kapton® film available from DuPont was used as the connecting substrate. The electrical connections were created by patterning the ultra-smooth 50 µm Kapton® film with standard photolithography, and depositing 200 nm of Au with 10 nm of Ti underneath as an adhesive layer on the film with an Angstrom E-beam Evaporator. The same steps were repeated on the second side. To combine the sensors, a small amount of H20E silver epoxy from EPO-TEK was added at the pads of the gold connections. The film was then placed onto a bump bonder along with one sensor. After aligning the sensor and the connections, a 2 kg force was placed between the chucks of the bump bonder, and the device was heated at approximately 150 degree Celsius for about 5 minutes. The same procedure is repeated to bond another sensor onto the other side of the film. The two sensors from this combination process are typically approximately parallel; in one example, using a 50 µm film, the filaments from two sensors were separated by a distance of approximately 40 µm.

Figure 4A:
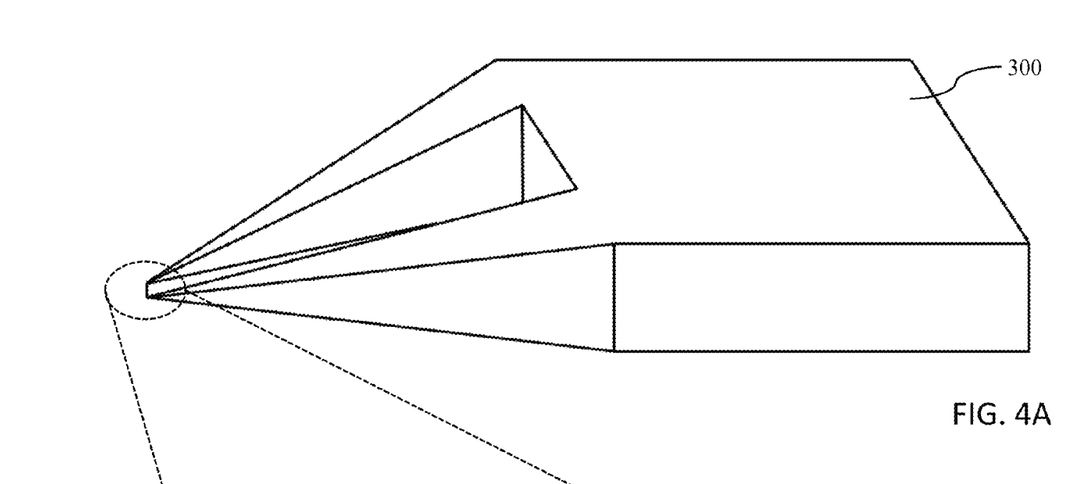
FIGS. 4A and 4B are block diagrams showing a NSTAP sensor configured with an angled wire filament.
Figure 4B:
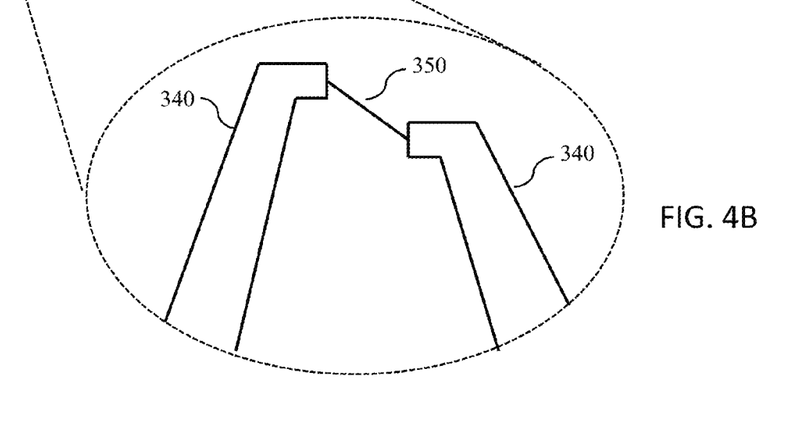
Figure 4C:
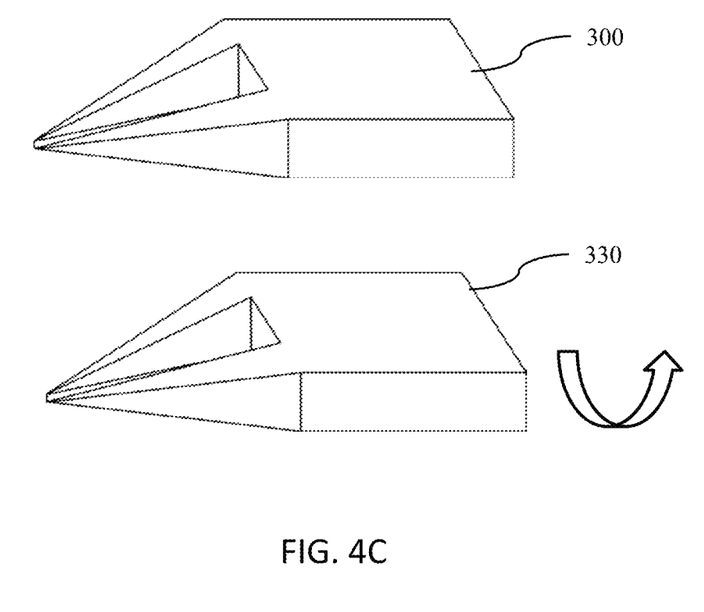
FIG. 4C is a side view of two NSTAP sensors configured in accordance with FIGS. 4A and 4B.
Figure 4D:
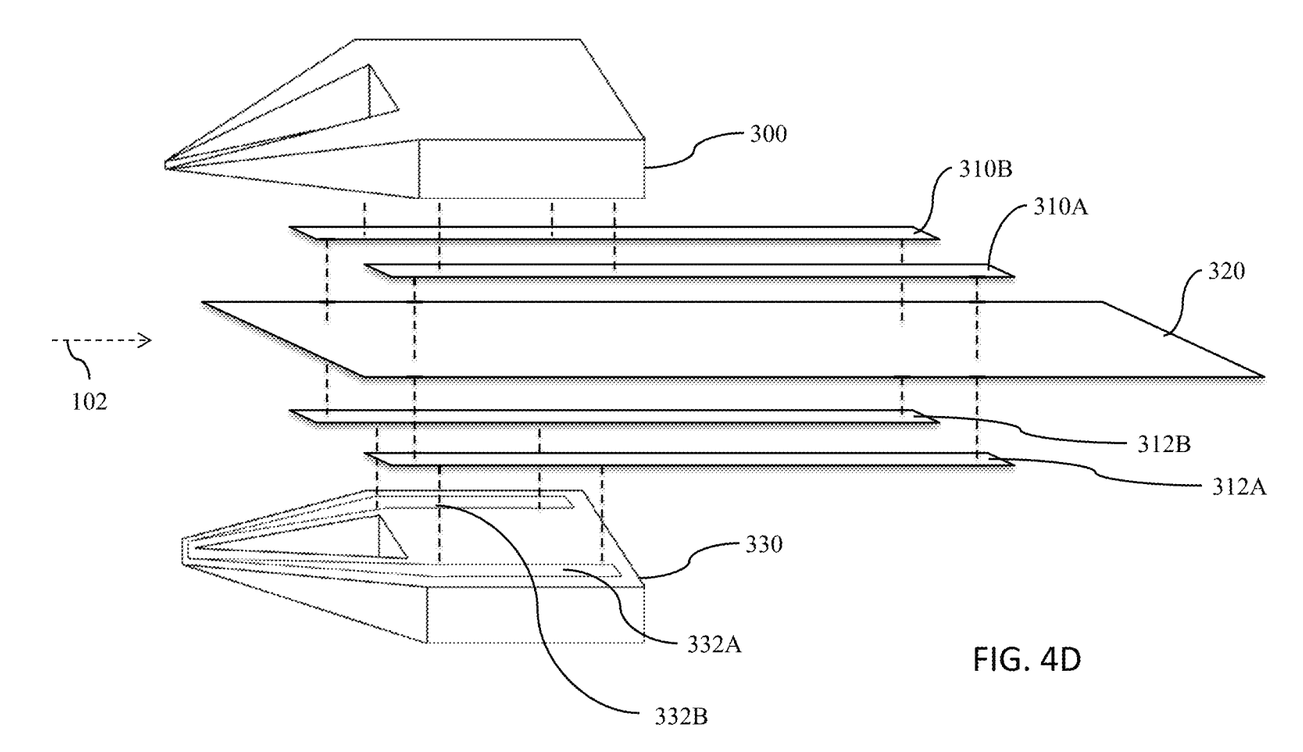
FIG. 4D is a side view showing the combination of two NSTAP sensors in accordance with FIGS. 4A-4C.

FIGS. 4A-4F illustrate examples of combining two NSTAP sensors with wire filaments that generally have a non-collinear orientation, e.g., an orthogonal orientation. As shown in FIGS. 4A and 4B, the NSTAP sensor 300 has pair of prongs 340 that are configured with an angular offset. For example, one or more prongs may be raised above or below the plane of the sensor body. The wire 350 filament is then angularly displaced from the plane of the sensor body. FIG. 4C is a side view of two NSTAP sensors 300 and 330 configured in accordance with FIGS. 4A and 4B. Sensor 330 is generally inverted as shown.

Figure 4E:
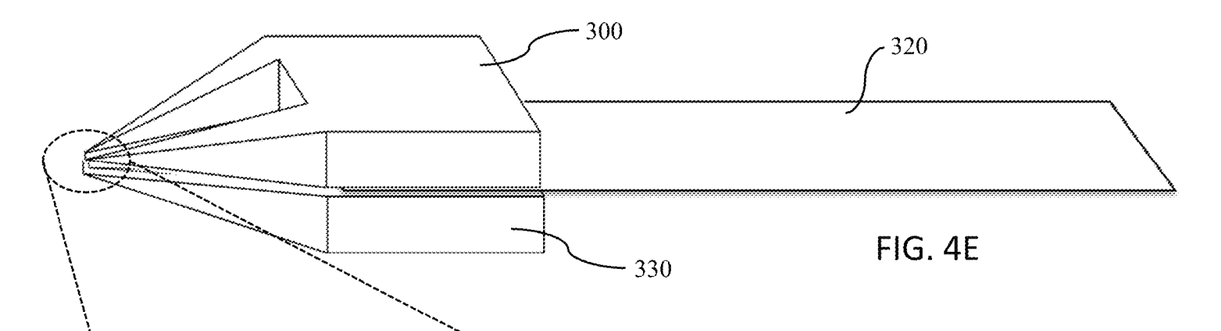
FIGS. 4E and 4F are block diagrams showing the assembled configuration of two NSTAP sensors configured in accordance with FIGS. 4A-4C.
Figure 4F:
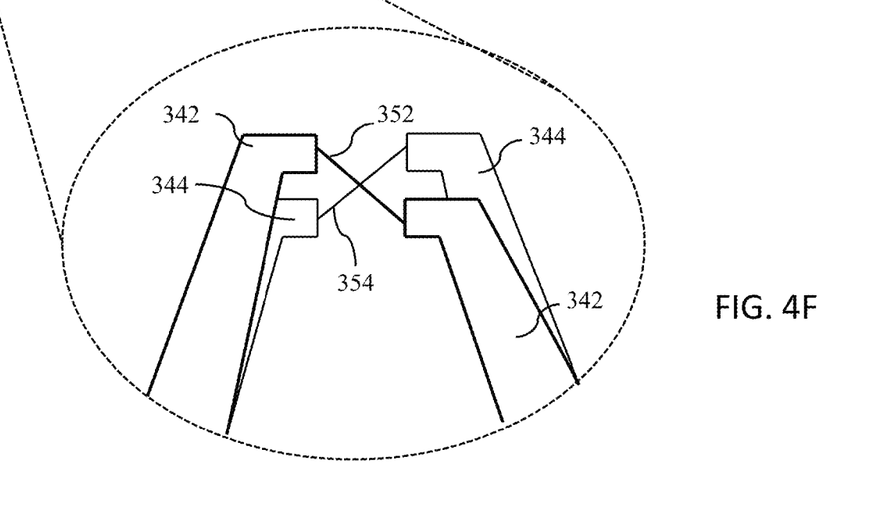

FIGS. 4E and 4F are block diagrams showing the assembled configuration of two NSTAP sensors configured in accordance with FIG. 4C. Two pairs of electrical connections 310A and 310B, 312A and 212B are formed on or applied to both sides of a thin electrically insulating coupling substrate 320 (typically a film) as discussed above in connection with FIGS. 2 and 3. The coupling substrate may be of any material appropriate for the design environment, such as a polyimide. NSTAP sensor 300 and NSTAP sensor 330 are then attached to the substrate, with a given sensor's prongs making contact with the connections on that side of the substrate. As shown in FIG. 44, the prongs 342, 344 of the two sensors 300 and 330 are positioned such that the wire filaments 352, 354 are locate one behind the other. In this example, the wire filaments 352, 354 are generally orthogonal with respect to each other. It should be understood that the wire filaments may be disposed other angular relationships without departing from the scope of this disclosure. This configuration also allows for measurement of temperature, velocity, and humidity with two different wire filament orientations in a measurement volume of less than 1 mm$^3$, e.g., 60 µm$^3$.

The disclosed NSTAP devices can be coupled to driving/measuring circuitry as generally shown by block 214 and may be operated in a constant voltage, constant current or a constant temperature mode. In any of these modes, the device can be used to measure any range of water content. Different configurations of NSTAP sensors may be combined as shown in FIGS. 2 and 3 and may be used for measurement of different parameters such as humidity, temperature or velocity. Such configurations may include sensors with different wire configurations and electrical operating conditions. For example, a first sensor may be configured with a Péclet number that is 1 or less (e.g., to reduce sensitivity to velocity) and a second sensor may be configured with a Péclet number that is greater than 1 (e.g., to increase sensitivity to velocity). A first sensor may be configured for a first humidity range and a second sensor may be configured for a second humidity range. It should be understood that a wide variety of configurations are possible based on the disclosure herein including any combination of sensors configured to detect humidity and/or temperature and/or velocity.

Figure 5:
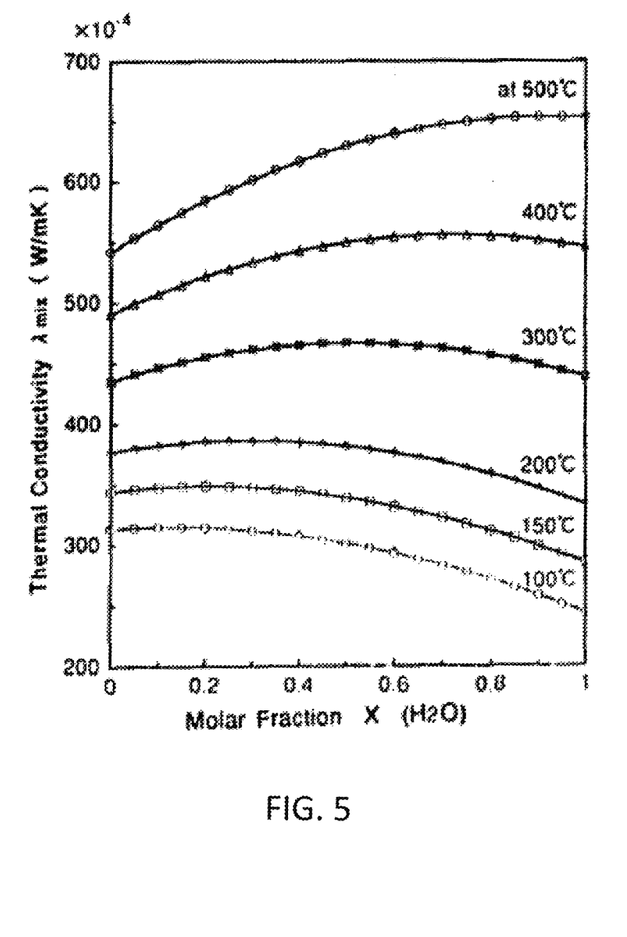
FIG. 5 is a graph of thermal conductivities of a typical fluid as a function of temperature and molar fraction of water.

FIG. 5 shows an example of a fluid thermal conductivity as a function of temperature and molar fraction of water. As seen in FIG. 5, the slope of the thermal conductivity curve at a given molar fraction of water is dependent on temperature. By adjusting the current flowing through the wire filament, a wire temperature can be reached that provides a desirable slope in the humidity range of interest. For example, using the graph in FIG. 4, for molar fractions of water greater than 0.6, a target wire temperature of 100° C. may be appropriate, as there is a significant slope in that region. At molar fractions of water below 0.2, however, using a target wire temperature of 100° C. would be less desirable, as the slope in that region is essentially flat. However, the slope in that region is significant, and therefore desirable, if the target temperature is 500° C.

Figure 6:
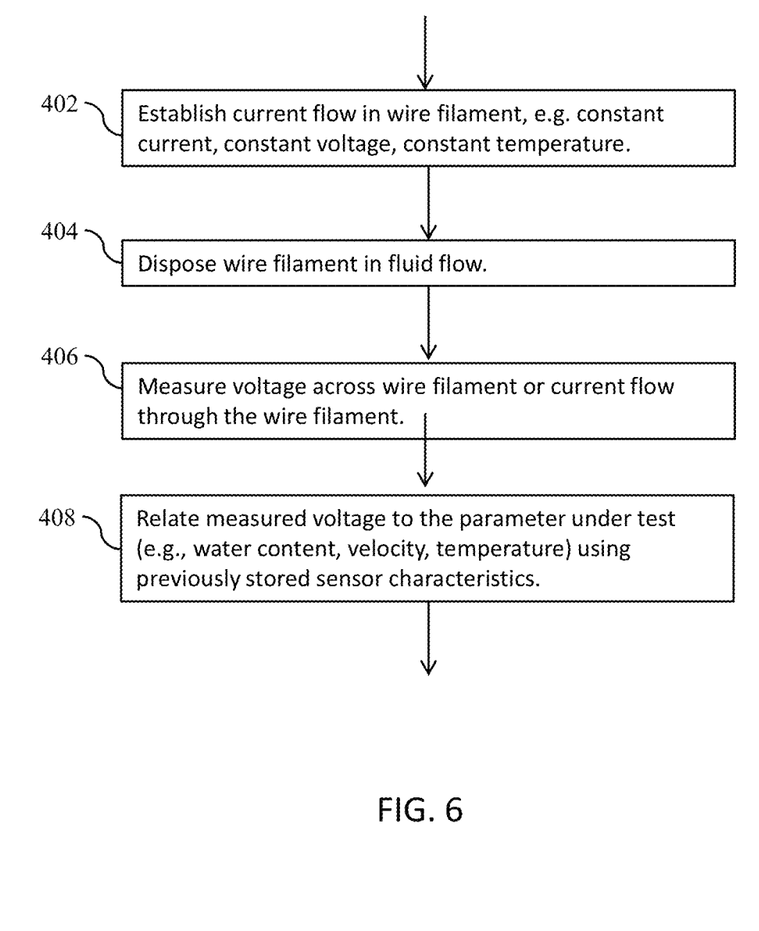
FIG. 6 is a flow chart showing a basic method of operation of one or more NSTAP sensors.

FIG. 6 is a flow chart generally showing the method of operating one or more of the devices disclosed above. In general, the disclosed devices may be used in hot wire anemometry systems and may be operated using conventional techniques. See e.g., H. H. Bruun, *Hot-wire Anemometry: Principles and Signal Analysis*, Oxford University Press, 1995 which is incorporated herein in its entirety. In operation, a current flow is established in the wire filament. The wire may be operated in a constant current, constant voltage or constant temperature mode as generally shown by block 402. In constant current mode, the driving/measuring circuitry, e.g., as generally shown by block 214 in FIG. 2, is configured to maintain a constant current flow in the wire filament. In constant voltage mode, the driving/measuring circuitry 214 is configured to maintain a constant voltage in the wire filament. In constant temperature mode, the driving/measuring circuitry 214 is configured to maintain a constant temperature in the wire filament.

The sensor is disposed in a fluid flow as generally shown by block 404. Depending on the mode of operation the measurement circuitry measures the voltage across or current flowing through wire filament as generally shown by block 406. The measured voltage/current is then correlated to the parameter under test (e.g., water content, velocity, temperature) using previously stored sensor characteristics as generally show by block 408.

Figure 7:
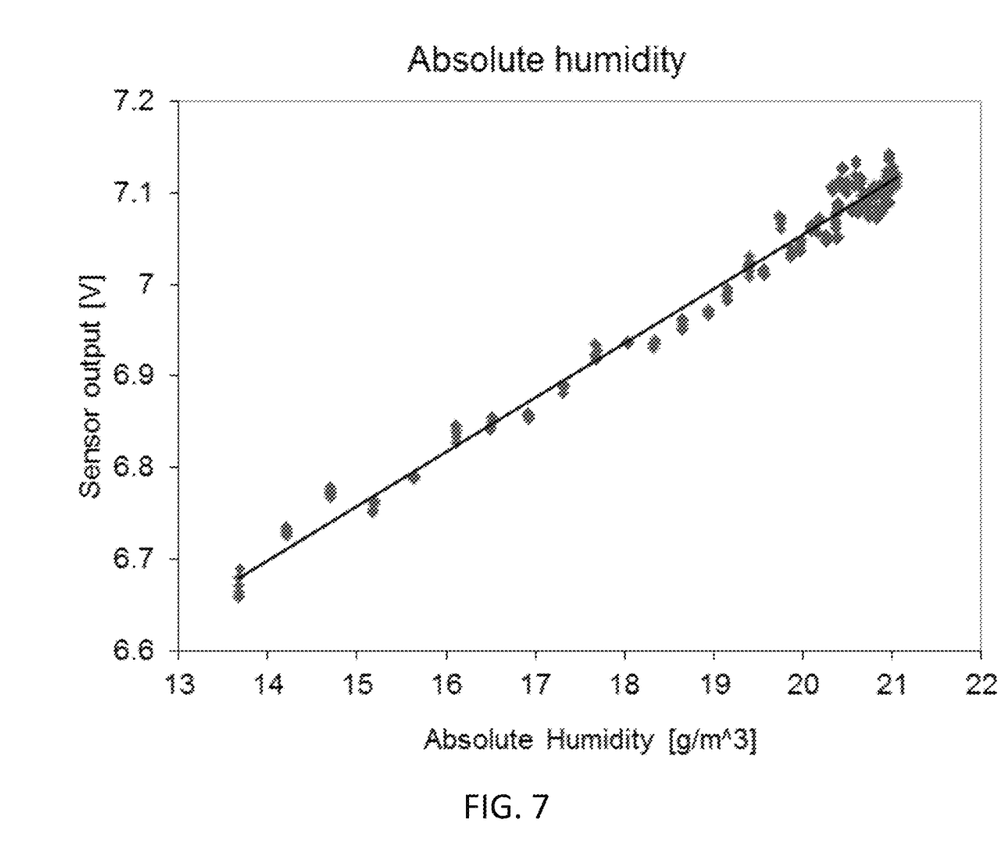
FIG. 7 is a table with sensor characteristics used to relate a voltage measured across a wire filament to a parameter under test.

FIG. 7 is a table with sensor characteristics that are used to relate a voltage measured across a wire filament to a parameter under test. In this example, the sensor voltage is correlated to absolute humidity. It should be understood that a wide variety of parameters may tested using the disclosed devices using the approach generally outlined above.

It should be understood that many variations are possible based on the disclosure herein. Although features and elements are described above in particular combinations, each feature or element can be used alone without the other features and elements or in various combinations with or without other features and elements.

What is claimed is:

1. A sensor system configured to measure water content of a fluid stream, the sensor system comprising:
    a wire filament configured with a Peclet number of 1 or less across a predetermined operating range of fluid velocities of the fluid stream, the wire filament being comprised of an electrically conductive material and further configured to have an electrical resistance which varies as a function of temperature;
    a pair of electrically conductive prongs coupled to opposite ends of the wire filament; and
    a measuring circuit configured to measure at least one of a voltage or a current of the sensor system,
    wherein the sensor system is further configured to correlate the at least one of a voltage or a current with at least one of a humidity or a thermal conductivity of the fluid stream using previously stored sensor characteristics.

2. The sensor system of claim 1, further comprising electrically conductive stubs coupled to the prongs.

3. The sensor system of claim 1, further comprising a structural support coupled to the prongs.

4. The sensor system of claim 3, wherein the structural support structure is comprised of silicon.

5. The sensor system of claim 1, wherein the wire filament is coupled to circuitry configured to supply an electric current to the wire filament to maintain the wire filament at one of an approximately constant current, an approximately constant voltage and an approximately constant temperature.

6. The sensor system of claim 1, wherein the wire filament is comprised of at least one of platinum and titanium.

7. The sensor system of claim 1, wherein the wire filament has at least one of a circular and rectangular cross section.

8. The sensor system of claim 1, wherein the prongs are tapered or shaped on one end to reduce aerodynamical interference.

9. The sensor system of claim 1, further comprising a second sensor having a second pair of electrically conductive prongs, the water content sensor being coupled to the second sensor by an electrically insulating connecting substrate.

10. The sensor system of claim 9, wherein the connecting substrate has opposite sides, each side being formed with electrical connections that are electrically coupled to the pair of electrically conductive prongs and second pair of electrically conductive prongs respectively.

11. A method of forming a sensor system configured to measure water content of a fluid stream, the method comprising:
    forming a wire filament configured with a Peclet number of 1 or less across a predetermined operating range of fluid velocities of the fluid stream, the wire filament being comprised of an electrically conductive material and further configured to have an electrical resistance which varies as a function of temperature;
    coupling the wire filament to a pair of electrically conductive prongs coupled to opposite ends of the wire filament;
    providing a measuring circuit to measure at least one of a voltage or a current of the sensor; and
    storing sensor characteristics relating to a correlation between the at least one of a voltage or a current with at least one of a humidity or a thermal conductivity of the fluid stream.

12. The method of claim 11, further comprising coupling electrically conductive stubs to the prongs.

13. The method of claim 11, further comprising forming a structural support coupled to the prongs.

14. The method of claim 13, wherein the structural support structure is comprised of silicon.

15. The method of claim 11, further comprising coupling the wire filament to circuitry configured to supply an electric current to the wire filament to maintain the wire filament at one of an approximately constant current, an approximately constant voltage and an approximately constant temperature.

16. The method of claim 11, wherein the wire filament is comprised of at least one of platinum and titanium.

17. The method of claim 11, further comprising forming the wire filament with at least one of a circular and rectangular cross section.

18. The method of claim 11, further comprising forming prongs that are tapered or shaped on one end to reduce aerodynamical interference.

19. The method of claim 11, further comprising providing a second sensor having a second pair of electrically conductive prongs, the water content sensor being coupled to the second sensor by an electrically insulating connecting substrate.

20. The method of claim 19, wherein the connecting substrate has opposite sides, each side being formed with electrical connections that are electrically coupled to the pair of electrically conductive prongs and second pair of electrically conductive prongs respectively.

21. A method of detecting water content in a fluid flow, the method comprising:
  establishing a current flow in a wire filament in a first sensor, the wire filament being configured with a Peclet number of 1 or less across a predetermined operating range of fluid velocities, the wire filament being comprised of an electrically conductive material and further configured to have an electrical resistance which varies as a function of temperature;
  disposing the wire filament in the fluid flow;
  measuring at least one of a voltage across or a current flowing through the wire filament; and
  correlating at least one of the measured voltage or current to at least one of a humidity or a thermal conductivity of the fluid flow using previously stored sensor characteristics.

* * * * *